United States Patent
Morgan

Patent Number: 5,888,066
Date of Patent: Mar. 30, 1999

[54] CONVERTER ASSEMBLY FOR THREADED DENTAL IMPLANTS

[75] Inventor: Vincent J. Morgan, Boston, Mass.

[73] Assignee: Diro, Inc., Boston, Mass.

[21] Appl. No.: 13,157

[22] Filed: Jan. 26, 1998

Related U.S. Application Data

[60] Provisional application No. 60/036,502, Jan. 28, 1998.

[51] Int. Cl.[6] .................................................. A61C 8/00
[52] U.S. Cl. ........................................ 433/172; 433/173
[58] Field of Search .................................. 433/172, 173, 433/174, 175, 176

[56] References Cited

U.S. PATENT DOCUMENTS

| | | | |
|---|---|---|---|
| 4,195,409 | 4/1980 | Child | 433/175 |
| 4,416,629 | 11/1983 | Mozsary et al. | 433/173 |
| 4,772,204 | 9/1988 | Soderberg | 433/174 |
| 5,114,343 | 5/1992 | Musikanti et al. | 433/173 |
| 5,174,755 | 12/1992 | Fukuda | 433/173 |
| 5,282,746 | 2/1994 | Sellers et al. | 433/172 |
| 5,597,306 | 1/1997 | Horlitz et al. | 433/173 |
| 5,662,475 | 9/1997 | Mena | 433/172 |
| 5,688,123 | 11/1997 | Meiers et al. | 433/173 |
| 5,733,124 | 3/1998 | Kwan | 433/173 |

Primary Examiner—Gene Mancene
Assistant Examiner—Pedro Philogene
Attorney, Agent, or Firm—John A. Haug

[57] ABSTRACT

A converter assembly for converting a dental implant having a threaded bore is shown having a cylindrical converter pin (22) with one end portion (24) threaded for reception in the threaded bore of the inplant. An opposite end portion (26) is formed with a locking taper which is receivable in a bore (34) of an abutment member (30) having a matching locking taper.

3 Claims, 1 Drawing Sheet

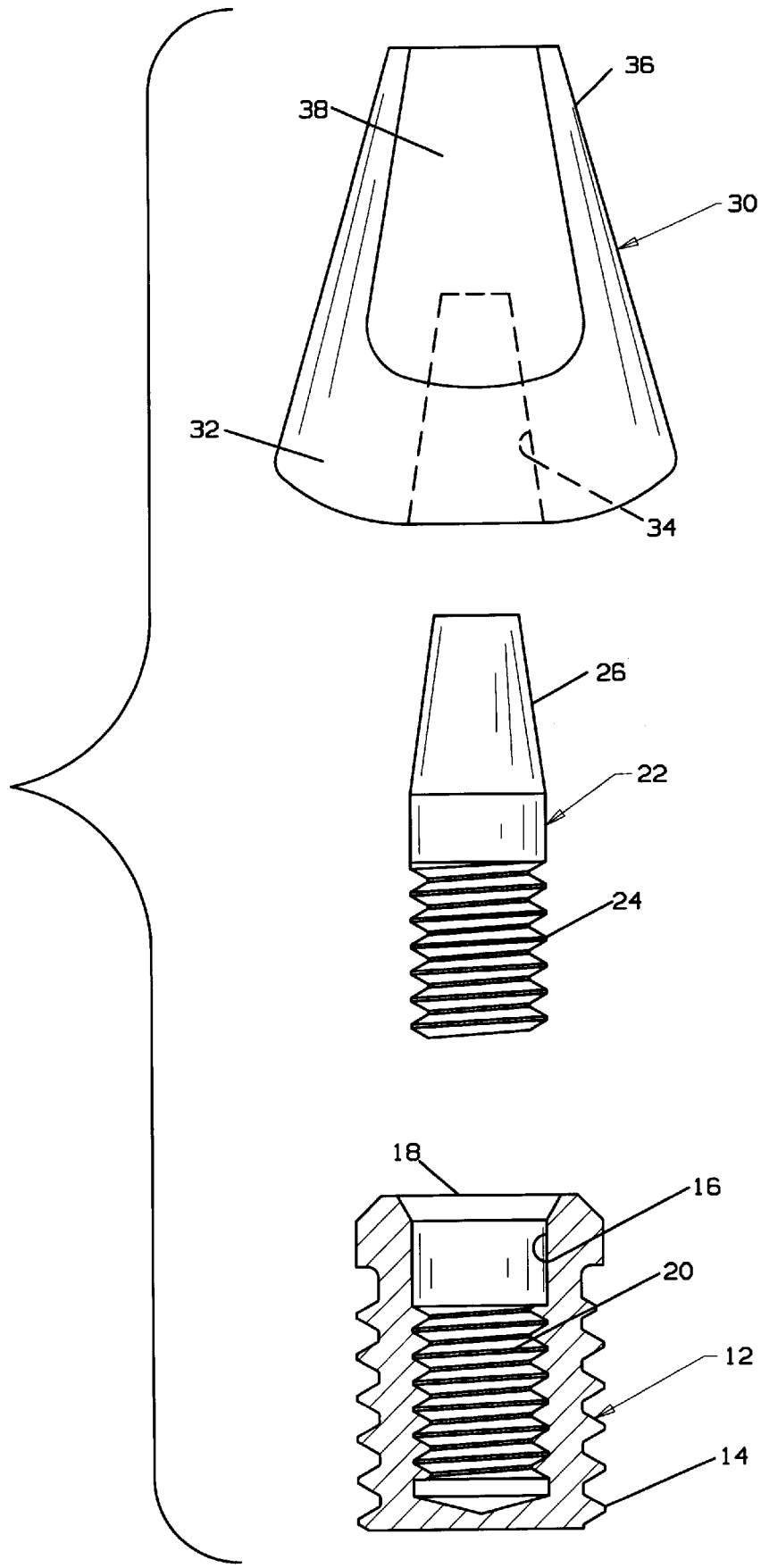

CONVERTER ASSEMBLY FOR THREADED DENTAL IMPLANTS

This application claims priority based on provisional application No. 60/036,502 filed Jan. 28, 1998.

BACKGROUND OF THE INVENTION

This invention relates generally to restorative dentistry and more particularly to dental implant systems. A common type of dental implant system comprises a generally cylindrical body made of biocompatible material and is formed with an outer surface configuration selected to promote osseointegration. For example, a plurality of fins which extend radially outwardly from the side wall of the body or an external thread formed in the side wall. A bore extends through a crestal end of the body along the longitudinal axis of the cylindrical body with at least a portion of the bore having an internal thread adapted to threadingly receive a variety of threaded copings, screws or other threaded posts of a dental prosthesis system.

One of the difficulties in using a threaded member to attach a prosthesis to the implant is the need for tight and lasting engagement of any threaded member received in the bore as well as the need for attaining a selected angular orientation, that is, the tooth simulating prosthesis must be positioned in a precise, given angular orientation. Any looseness between the components can eventually result in breakage due to the lateral forces placed on the components during chewing.

Another type of dental implant system has a smooth circular bore formed with a locking taper for reception of a post of an abutment having a matching locking taper. A system of this type is described and claimed in U.S. Pat. No. 4,738,623, the subject matter of which is incorporated herein by this reference. This type of system has several inherent, distinct advantages over the threaded system described above including the ability to precisely position an abutment in any selected angular orientation and, once tapped into locking engagement, characterized in having complete absence of motion between the implant and the abutment member. This results in fewer implant failures. Yet another advantage of a locking taper system is that a locking taper connection forms a bacterial seal as opposed to a threaded system which inherently has a space between the male and female threads which can be accessed by bacteria. Thus the locking taper system results in better soft tissue health in tissue proximate to the implant site.

It would be desirable, particularly in situations where a user of a threaded system who has had problems with implant failures involving breakage of the abutment member, to be able to convert from a threaded system to a locking taper system however, using presently available procedures and components, this requires removal of the threaded implant and replacement with a locking taper implant with a concomitant healing period of some months.

SUMMARY OF THE INVENTION

It is an object of the present invention to provide apparatus for converting a threaded implant system having critical angular orientation requirements for the positioning of an abutment while at the same time providing a rigid attachment between the abutment and the implant to a system in which an abutment can be easily oriented and securely attached to the implant. It is another object to overcome the prior art limitations noted above.

Briefly described, in accordance with the invention, an elongated converter pin is provided with an external threaded portion at one end portion and a locking taper at an opposite end portion. The length of the converter pin is selected so that the locking taper portion extends out of the threaded implant when the threaded portion of the converter pin is completely screwed into the threaded bore of the implant. An abutment component is provided with a bore formed with a matching locking taper extending into a base portion thereof. The converter pin is threaded into the implant bore, preferably cemented therein, and the abutment is positioned on the locking taper portion of the converter pin in an appropriate selected angular orientation and is then tapped into locking, immobile engagement. The abutment may be a tooth-simulating prothesis itself or, preferably, may have a non-circular outer, upper surface configuration suitable for mounting thereon a conventional tooth simulating crown or the like in a conventional manner.

Additional objects, advantages and features of the novel and improved attachment system of this invention will be set forth in part in the description which follows and in part will be obvious from the description.

BRIEF DESCRIPTION OF THE DRAWINGS

The accompanying drawing, which is incorporated in and constitutes part of the specification, illustrates a preferred embodiment of the invention and, together with the description, serves to explain the objects, advantages and principles of the invention. Dimensions may have been altered for purposes of illustration.

The sole FIGURE of the drawing is an exploded front elevational view, partly in cross section, of a threaded dental implant with a locking taper converter pin and an abutment made in accordance with the invention.

DETAILED DESCRIPTION OF PREFERRED EMBODIMENT

A conventional dental implant 12 is shown comprising a generally cylindrical body made of biocompatible material having an outer surface configuration suitable for promoting osseointegration when placed in a prepared bore in the aveolar ridge of an individual. As shown, implant 12 is formed with an external thread 14 for this purpose however other configurations could be employed, such as a plurality of fins or the like. A bore 16 is formed through the crestal end 18 of the implant and is provided with an internal thread 20 over at least a portion of its length for reception of any one of various threaded members, such as copings, or a screw or the like of an abutment for a dental prosthesis.

According to the invention a converter pin 22 comprises an elongated cylindrical member, formed of suitable material such as titanium or titanium alloy, preferably the same material as that used for implant 12 and abutment 30 to be described. The converter pin has a first end portion 24 of an appropriate diameter and is formed with an external thread selected to be threadingly received in bore 16 of implant 12. Converter pin 22 has an opposite end portion 26 formed with a locking taper such as that described in U.S. Pat. No. 4,738,623 mentioned above. The length of the converter pin is selected so that locking taper portion 26 extends above crestal end 18 when the pin is screwed into bore 16. An abutment member 30 has a base portion 32, preferably formed as a segment of a spherical surface and formed with a bore 34 having a locking taper matching that of end portion 26 of pin 22. Abutment 30 is preferably formed with an anti-rotational outer upper surface 36 as by providing one or more flat surfaces 38 so that a dental crown or the like can be fixedly mounted thereon in a conventional manner. It will be appreciated that abutment 30 may be of various types and could even be a tooth-simulating prosthesis itself as long as it is provided with bore 34 having a locking taper matching that of the converter pin.

Once threaded end portion 24 is screwed into bore 16 and, if desired, fixedly cemented therein, abutment 30 can be placed on end portion 26 with the angular position thereof adjusted to any selected orientation and then tapped into locking engagement with converter pin 20.

Although the invention has been described with regard to specific preferred embodiments thereof, variations and modifications will become apparent to those skilled in the art. For example, end portion 26 of converter pin 22 could be formed having a bore with a locking taper for reception of a mating male member having a corresponding taper. It is therefore the intention that the appended claims be interpreted as broadly as possible in view of the prior art to include all such variations and modifications.

What is claimed:

1. In a dental implant system having a body formed of biocompatible material having a longitudinal axis and having a crestal end formed with a threaded bore extending along the longitudinal axis from the crestal end into the body, a converter assembly comprising an elongated converter pin having first and second end portions, a thread formed at the first end portion for threading reception in the threaded bore of the implant and a locking taper formed at the second end portion, the first end portion having a length selected so that the second end portion projects beyond the crestal end of the implant when the first end portion is screwed into the threaded bore of the implant and an abutment member having a base portion formed with a bore having a suitable size and a matching locking taper for reception of the second end portion of the converter pin in direct engagement with the abutment member.

2. A dental inplant system according to claim 1 in which the abutment member has a longitudinal axis and the base portion of the abutment member is configured generally as a segment of a sphere and an upper portion is provided with a configuration such that a cross section, taken perpendicular to the longitudinal axis, is non-circular.

3. A converter assembly for use with a dental implant having a threaded bore comprising an elongated converter pin having first and second end portions, a thread formed at the first end portion for threading reception in a threaded bore of an implant and a locking taper formed at the second end portion and an abutment member having a base portion formed with a bore having a suitable size and a matching locking taper matching that of the converter pin for reception of the second end portion of the converter pin in the bore in direct engagement with the abutment member.

* * * * *